(12) United States Patent
Schmitt

(10) Patent No.: US 10,772,941 B2
(45) Date of Patent: Sep. 15, 2020

(54) PROCESS AND COMPOSITION FOR LOW DOSE INSEMINATION

(71) Applicant: IMV TECHNOLOGIES, L'Aigle (FR)

(72) Inventor: Eric Schmitt, Villaines-la-Juhel (FR)

(73) Assignee: IMV TECHNOLOGIES, L'Aigle (FR)

( * ) Notice: Subject to any disclaimer, the term of this patent is extended or adjusted under 35 U.S.C. 154(b) by 311 days.

(21) Appl. No.: 15/746,495

(22) PCT Filed: Jul. 14, 2016

(86) PCT No.: PCT/EP2016/066815
§ 371 (c)(1),
(2) Date: Jan. 22, 2018

(87) PCT Pub. No.: WO2017/012993
PCT Pub. Date: Jan. 26, 2017

(65) Prior Publication Data
US 2018/0200345 A1  Jul. 19, 2018

(30) Foreign Application Priority Data

Jul. 23, 2015 (EP) .................................. 15306202

(51) Int. Cl.
| | | |
|---|---|---|
| *A61K 38/47* | (2006.01) | |
| *A61K 38/16* | (2006.01) | |
| *A61K 35/52* | (2015.01) | |
| *A61D 19/02* | (2006.01) | |
| *A61K 9/00* | (2006.01) | |

(52) U.S. Cl.
CPC .............. *A61K 38/47* (2013.01); *A61D 19/02* (2013.01); *A61K 9/0034* (2013.01); *A61K 35/52* (2013.01); *A61K 38/168* (2013.01); *C12Y 302/01018* (2013.01)

(58) Field of Classification Search
CPC ...... A61B 17/43; A61K 38/47; A61K 9/0034; A61K 35/52; A61D 19/02
USPC .......................................................... 600/35
See application file for complete search history.

(56) References Cited

U.S. PATENT DOCUMENTS

| | | |
|---|---|---|
| 5,135,759 A | 8/1992 | Johnson |
| 5,766,632 A | 6/1998 | Oldham et al. |
| 5,972,592 A | 10/1999 | Suarez |
| 2012/0329035 A1 | 12/2012 | Hudson et al. |

FOREIGN PATENT DOCUMENTS

| | | |
|---|---|---|
| WO | 2009045555 A1 | 4/2009 |
| WO | 2010149739 A1 | 12/2010 |

OTHER PUBLICATIONS

Calvete, Juan J. et al., "Boar Spermadhesins AQN-1 and AQN-3: Oligosaccharide and Zona Pellucida Binding Characteristics", Biol. Chem., vol. 377, pp. 521-527, Jul./Aug. 1996.
Dostalova, Zuzana et al., "Boar spermadhesin AWN-1: Oligosaccharide and zona pellucida binding characteristics", Eur. J. Biochem., vol. 230, pp. 329-336, Feb. 1995.
Ekhlasi-Hundrieser, Mahnaz et al., "Spermadhesin AQN1 Is a Candidate Receptor Molecule Involved in the Formation of the Oviductal Sperm Reservoir in the Pig", Biology of Reproduction, vol. 73, pp. 536-545, May 11, 2005.
Goncalves, RF. et al., "Influence of Osteopontin in Bovine Uterine Tube Fluid on Sperm Binding and Fertilization in RCA-1 Lectin-treated Oocytes", Reprod. Dom. Anim., vol. 44, pp. 152-155, 2009.
Green, C.E. et al., "Carbohydrate mediation of boar sperm binding to oviductal epithelial cells in vitro", Journal of Reproduction, vol. 122, pp. 305-315, 2001.
Krueger, C. and Rath, D. "Intrauterine insemination in sows with reduced sperm number", Reprod. Fertil. Dev., vol. 12, pp. 113-117, 2000.
Srivastava, Prakash et al., "Neurominidase Induces Capacitation and Acrosome Reaction in Mammalian Spermatozoa", The Journal of Experimental Zoology, vol. 245, pp. 106-110, 1988.
Taylor, U. et al., "Binding of porcine spermatozoa to uterine epithelial cells modulates the female immune response and might indicate the formation of a pre-oviductal sperm reservoir", Soc. Reprod. Fertil. Suppl., vol. 66, pp. 83-84, 2009.
Bohmerova, Eva, International Search Report for Application No. PCT/EP2016/066815, dated Sep. 26, 2016.

*Primary Examiner* — John P Lacyk
(74) *Attorney, Agent, or Firm* — Greer, Burns & Crain, Ltd.; Steven P. Fallon

(57) ABSTRACT

The present invention relates to a composition for use in low dose artificial insemination and to a process for artificial insemination of a female mammal using a dose of sperm originating from a male mammal of the same species that is significantly lower than necessary in the absence of the composition. The preferred female mammal is a sow (*Sus scrofa*), and preferably the composition is for use in artificial uterine insemination, and the process for artificial insemination preferably is uterine insemination.

19 Claims, 4 Drawing Sheets

PROCESS AND COMPOSITION FOR LOW DOSE INSEMINATION

Figure 1:
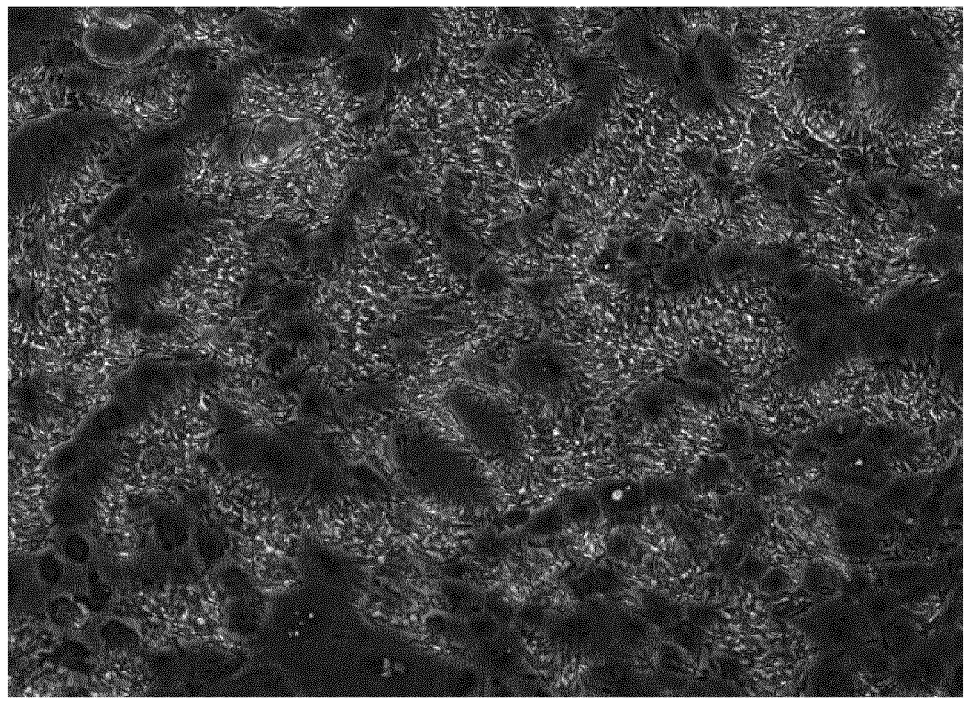

The present invention relates to a composition for use in low dose artificial insemination and to a process for artificial insemination of a female mammal using a dose of sperm originating from a male mammal of the same species that is significantly lower than necessary in the absence of the composition. The preferred female mammal is a sow (*Sus scrofa*), and preferably the composition is for use in artificial uterine insemination, and the process for artificial insemination preferably is uterine insemination.

STATE OF THE ART

For conventional artificial insemination of sows, fresh boar sperm is used in a dose of approx. 1 to $3\times10^9$ sperm in a volume of 100 mL diluent, twice within 24 h into the uterus, and frozen sperm is used in a dose of approx. $5\times10^9$ sperm. A boar ejaculate can therefore be divided into 5 to 30 doses of fresh sperm. Usually, this conventional artificial insemination performed for the first time around 24 h prior to ovulation, observed as standing heat.

Using invasive processes, e.g. surgical laparoscopy, sperm doses as low as $1\times10^7$ frozen-thawed sperm can be deposited directly into the sow's oviduct for fertilization.

U.S. Pat. No. 5,135,759 A describes a FACS device and process for sex-chromosome specific sorting of sperm cells into fractions predominantly containing X-chromosome or Y-chromosome bearing sperm.

WO 2010/0149739 A1 describes a FACS device and process using a laser for deflecting fluid sections containing sperm for sorting into fractions predominantly containing X-chromosome or Y-chromosome bearing sperm.

Green et al., Reproduction 122, 305-315 (2001) describe that carbohydrate glycans mediate boar sperm binding to oviduct epithelial cells.

Ekhlasi-Hundrieser et al., Biol Reprod 73, 536-545 (2005) describe that the sperm adhesion AQN-1 is a candidate receptor for forming a sperm reservoir in the oviduct of the sow.

Dostalova et al., Eur J Biochem 230, 329-336 (1995), Calvete et al., Biol Chem 377, 521-527 (1996) describe that the sperm adhesins AQN-1 and AQN-3 show an affinity like AWN for the zona pellucida glycoproteins.

Krueger and Rath, Reprod Fertil Dev. 12, 113-117 describe that very low doses of laparotomically administered sperm into the tip of the uterine horn resulted in pregnancies.

Taylor et al., Soc Reprod Fertil Suppl 66, 83-84 (2009) describe that porcine sperm bind to uterine epithelial cells.

OBJECT OF THE INVENTION

It is an object of the invention to provide a composition for use in artificial insemination, especially for uterine insemination that allows for fertilization by a significantly lower sperm dose. The process of artificial insemination should avoid any surgical steps, and should preferably comprise or consist of the application of the sperm insemination dose by classic artificial insemination, e.g. by uterine body application in sows.

DESCRIPTION OF THE INVENTION

The invention achieves the object by the features of the claims, especially in a first variant by contacting the sperm with a binding agent having affinity for N-acetyl glucosamine (Glc-NAc) and/or affinity for sialic acid, and/or affinity for mannose, and/or with an agent hydrolysing sialic acid and/or hydrolysing N-acetyl glucosamine and/or hydrolysing oligo mannose, e.g. prior to or concurrent to introducing the sperm into the uterus of the female mammal, and in a second variant, contacting the uterus with a binding agent having affinity for sialic acid and/or having affinity for β-D(1,3)-galactosamine and/or with an agent hydrolysing sialic acid, and/or contacting with sialic acid and/or N-acetyl glucosamine and/or oligo mannose or mannose, e.g. prior to or concurrent to introducing the sperm into the uterus of the female mammal. The first and second variants can be separate or combined.

In the first variant, in a first embodiment, contacting of the sperm with at least one of these compounds can be made by providing a composition for artificial insemination, also termed a liquid formulation, the composition containing the sperm, wherein the composition contains at least one of these compounds. Preferably, the composition contains the sperm in a dose, which is significantly lower than the dose used for conventional artificial insemination.

In the first variant, in a second embodiment, the sperm can be contacted with at least one of these compounds, be separated from unbound portions of these compounds, e.g. by mixing the sperm with at least one of these compounds and washing the sperm, e.g. by centrifugation to collect the sperm from the suspension containing the at least one of these compounds and transfer of the sperm to a liquid composition which is free from the at least one of these compounds, which liquid composition e.g. is suitable for insemination, e.g. for use as at least one insemination dose.

In the first variant, in a third embodiment, the at least one of these compounds for contacting the sperm can be provided as a composition for administration to the genital tract of the female prior to or concurrent with the introduction of the sperm that is contained in a separated liquid composition.

In the second variant, in a fourth embodiment, at least one compound for contacting the uterus can be provided as a composition for administration to the genital tract of the female, especially to the uterus, prior to or concurrent with the introduction of the sperm that is contained in a separated liquid composition.

In the second variant, in a fifth embodiment, at least one compound for contacting the uterus can be provided in a composition containing the sperm dose.

Embodiments, in which the process comprises the administration of a composition prior to introduction of sperm into the female, e.g. wherein the composition does not contain sperm, the process serves to prepare the female for artificial insemination. Therein, the artificial insemination can occur following the administration of the composition, e.g. by subsequent introduction of sperm into the uterus.

Preferably, the female mammal is a gilt or a sow and the sperm is boar sperm, fresh or frozen. In a variant, gender-enriched sperm, e.g. boar sperm doses, e.g. sex-chromosome specifically sorted sperm, are used either fresh or frozen, preferably thawed from the frozen state.

The invention is based on the finding that at least in the porcine, fertile sperm is bound to a significant extent to the uterine epithelium, especially to the endometrium, exemplified by uterine epithelial cells, and that reducing the binding of sperm to the uterine epithelium results in fertilisation by a lower dose of sperm used for artificial insemination. For reducing the binding of sperm to the uterine epithelium, the binding ligand of the sperm mediating binding to the endometrium can be masked, e.g. by contacting the sperm with a binding agent having affinity for N-acetyl glucosamine (Glc-NAc) and/or affinity for sialic acid, which binding agent can e.g. be a lectin or an antibody, and/or by contacting the sperm with an enzyme hydrolysing sialic acid and/or hydrolysing N-acetyl glucosamine, e.g. a sialidase for hydrolysing sialic acid. In the alternative or in addition, the endometrium can be contacted with a binding agent having affinity for sialic acid and/or having affinity for β-D(1,3)-galactosamine, which binding agent can e.g. be a lectin or an antibody, and/or with an agent hydrolysing sialic acid, and/or contacting with sialic acid and/or N-acetyl glucosamine and/or oligo mannose or mannose. In a further alternative, the sperm can be contacted with sialic acid and/or β-D(1,3)-galactosamine. Preferably, the lectin, sialidase and antibody are natural molecules, e.g. not chemically modified, especially not modified by a PEG moiety.

The reduction of the binding of sperm to the endometrium was observed when masking N-acetyl glucosamine (Glc-NAc) and/or sialic acid and/or oligo mannose or mannose on the sperm and/or on the endometrial cells, or removing these molecules from sperm and/or from endometrial cells, and/or contacting the sperm and/or the uterus with N-acetyl glucosamine (Glc-NAc) and/or sialic acid and/or oligo mannose or mannose, resulting e.g. in a saturation of the molecules binding these. These observations can be interpreted to the end that at least in the porcine, the binding of sperm to the endometrium is mediated by the interaction of N-acetyl glucosamine and/or sialic acid and/or mannose and/or glucose present on the sperm, especially on the sperm head, and is also mediated by sialic acid and/or β-D(1,3)-galactosamine present on the endometrium.

As the compositions and processes according to the invention allow for the fertilisation of a female mammal, especially of a non-human female mammal, preferably a sow, by a significantly reduced number of sperm compared to conventional artificial insemination, the binding agent having affinity for N-acetyl glucosamine (Glc-NAc) and/or having affinity for sialic acid, and/or having affinity for mannose, and/or an agent hydrolysing sialic acid and/or hydrolysing N-acetyl glucosamine and/or an agent hydrolysing oligo mannose, e.g. prior to or concurrent to introducing the sperm into the uterus of the female mammal, and in a second variant, a binding agent having affinity for sialic acid and/or having affinity for β-D(1,3)-galactosamine and/or with an agent hydrolysing sialic acid, and/or sialic acid and/or N-acetyl glucosamine and/or oligo mannose or mannose for contacting the uterus, these compositions act as pharmaceutical active compounds in enhancing the fertilisation at lower numbers of sperm compared to conventional artificial insemination. Accordingly, the composition is for use in enhancing the fertility of an artificial insemination sperm dose, especially for administration to the genital tract of the female, e.g. to the uterus prior to or concurrent to introduction of sperm, and/or by contacting the sperm with the composition, especially prior to or concurrent to introduction of sperm into the female genital tract, e.g. into the uterus, especially into the short uterine body of a sow.

Herein, doses given for sperm relate to live sperm in the dose. Preferably, the dose for artificial insemination according to the invention is lower by a factor of at least 5, preferably by a factor of at least 10, more preferably by a factor of at least 20 or at least by a factor of 30, more preferably at least by a factor of 50 or by at least a factor of 100, compared to the dose for use in conventional artificial insemination, wherein in conventional insemination the sperm is suspended in a synthetic medium not containing the compound, and wherein both in the dose according to the invention and in the dose for conventional artificial insemination the sperm is fresh, i.e. non-frozen, or frozen. For example, for sows (Sus scrofa), a dose for conventional artificial insemination contains approx. 1 to $3\times10^9$ for fresh sperm (Colenbrander et al., Reprod Domest Anim 1, 298-333 (1991)), and approx. $5\times10^9$ for frozen sperm, which prior to insemination is generally thawed. Generally preferred, the insemination is at least at 24 h prior to ovulation, e.g. observed as standing heat.

Preferably, a dose for artificial insemination can contain $0.4\times10^9$, preferably $0.2\times10^9$, more preferably $100\times10^6$ or $66\times10^6$, more preferably $40\times10^6$ or $20\times10^6$ for fresh sperm, and $1\times10^9$, preferably $0.5\times10^9$, more preferably $250\times10^6$ or $165\times10^6$, more preferably $100\times10^6$ or $50\times10^6$ for frozen sperm, respectively.

The fertility obtained by the compositions and processes according to the invention and in conventional artificial insemination, respectively, is preferably determined as the sum of fertilisation rate, farrowing rate and weaning rate, e.g. as described in Vazquez et al., Theriogenology 63, 536-547 (2005).

Optionally, the sperm is predominantly X-chromosome bearing sperm, e.g. obtained by sex-chromosome specific sorting.

The dose can e.g. comprise a volume of 80 to 100 mL.

The binding agent can be comprised e.g. in the dose in an amount of from 0.1-1 or 1.0 to 5.0 µg/ml.

Preferably, the sperm dose can contain at least one binding agent having affinity for N-acetyl glucosamine (Glc-NAc) and/or having affinity for sialic acid, which binding agent can e.g. be a lectin or an antibody, and/or can contain an enzyme hydrolysing sialic acid and/or hydrolysing N-acetyl glucosamine, e.g. a sialidase for hydrolysing sialic acid. Optionally, in the alternative, the sperm dose can contain N-acetyl glucosamine (Glc-NAc), sialic acid and/or oligo mannose and/or mannose.

Optionally, the at least one binding agent having affinity for N-acetyl glucosamine (Glc-NAc) and/or having affinity for sialic acid, which binding agent can e.g. be a lectin or an antibody, and/or an enzyme hydrolysing sialic acid and/or hydrolysing N-acetyl glucosamine, e.g. a sialidase for hydrolysing sialic acid, can be administered to the genital tract of the female, e.g. to the cervix, preferably to the uterus, in advance of the introduction of the sperm, e.g. by insemination.

Most preferably, the composition and process of the invention contain a binding agent having affinity for N-acetyl glucosamine and/or affinity for sialic acid, especially a lectin or antibody binding to N-acetyl glucosamine and/or affinity for sialic acid, and/or an enzyme hydrolysing sialic acid, e.g. a sialidase. These compositions and processes have the advantage of not interfering or interfering only to an acceptable low level, with the binding of the sperm to the zona pellucida, which binding is generally assumed to at least in part depend on the binding of mannose containing ligands on the zona pellucida.

Figure 2A:
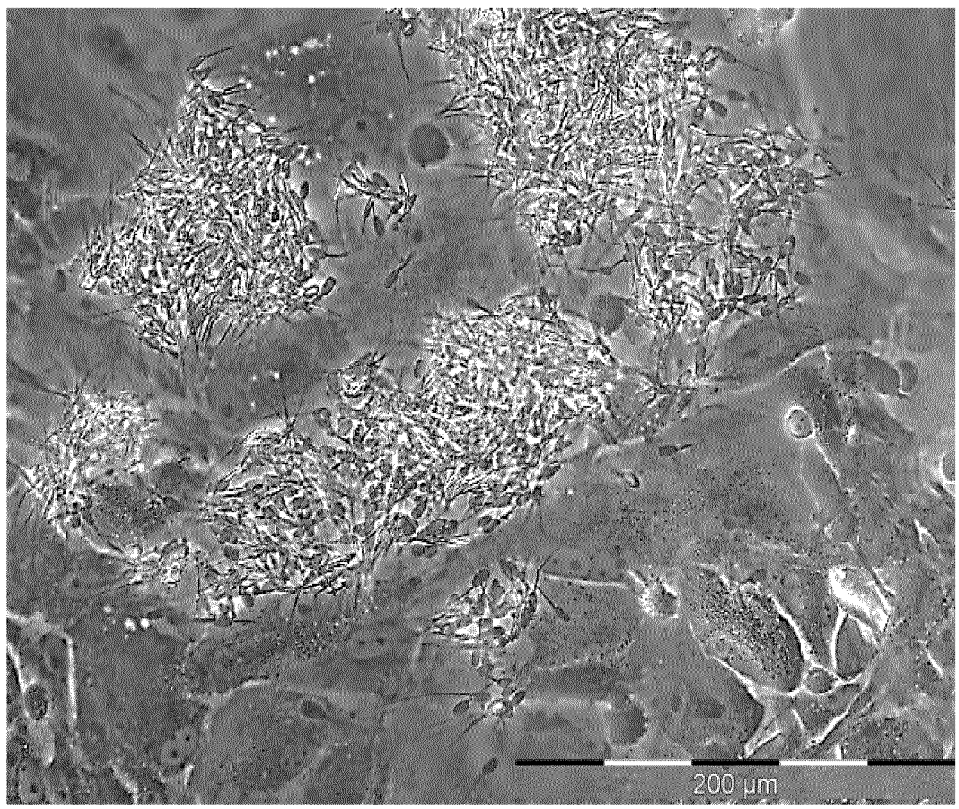
Figure 2B:
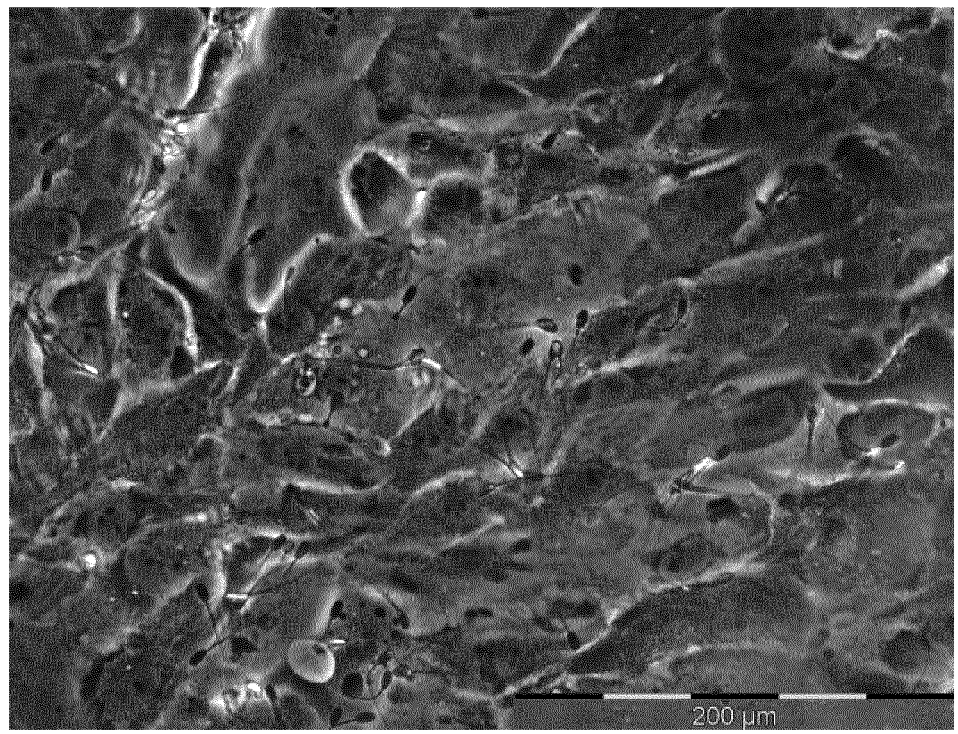
Figure 3A:
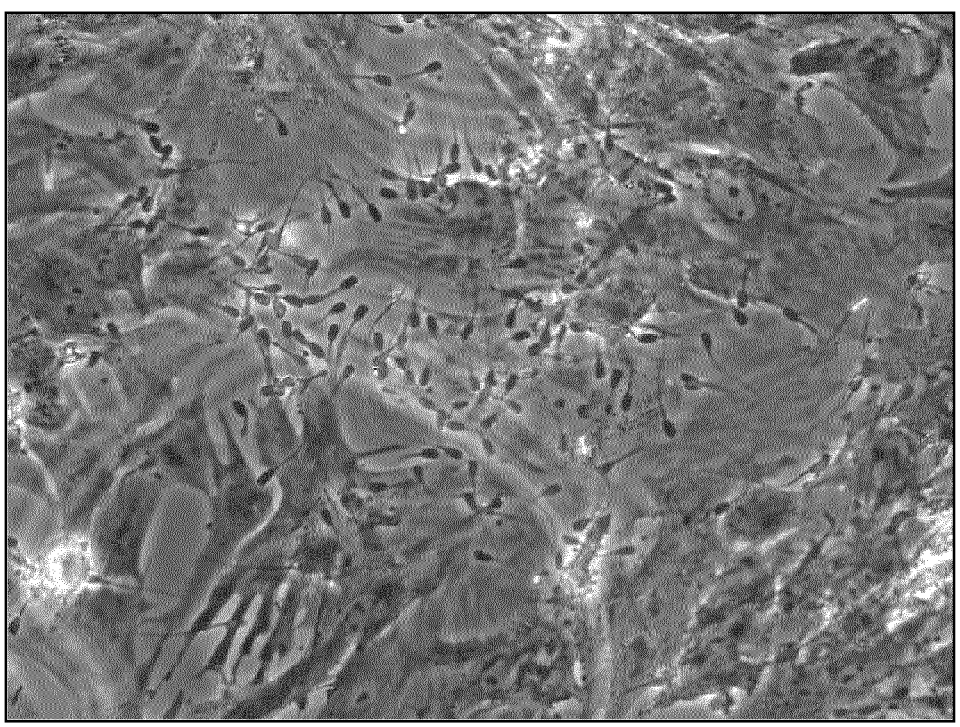
Figure 3B:
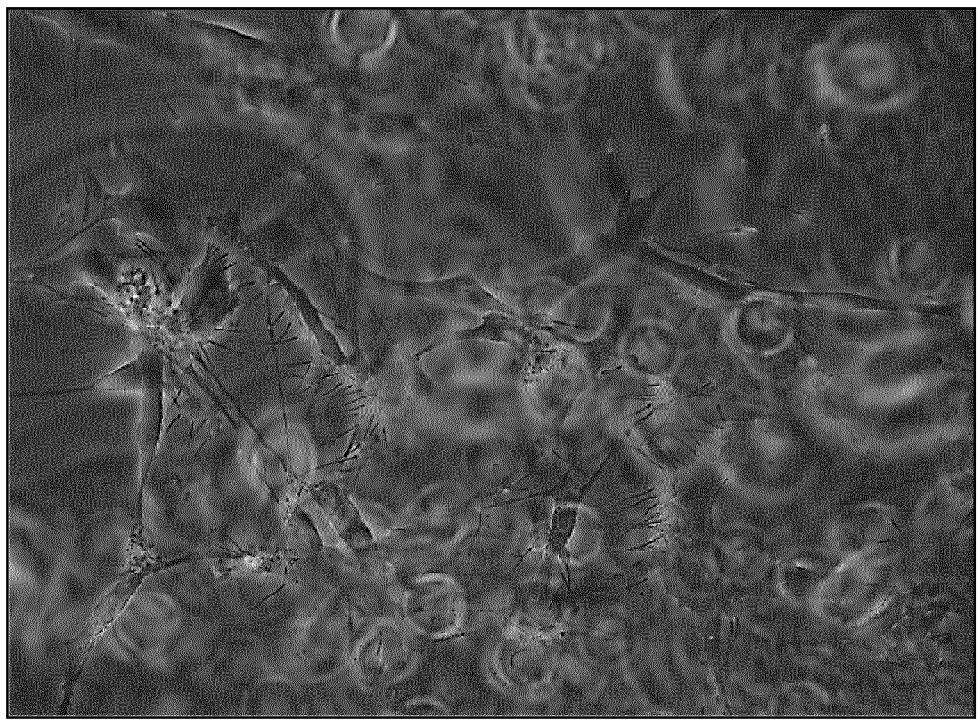

The invention is now described in greater detail by way of examples with reference to the figures, which show in FIG. 1 a confocal micrograph of porcine sperm after 10 min co-incubation with a cultivated UEC monolayer, FIG. 2A a confocal micrograph of porcine sperm after pre-treatment with ConA after 10 min co-incubation with a cultivated UEC monolayer, FIG. 2B a confocal micrograph of porcine sperm after pre-treatment with WGA after 10 min co-incubation with a cultivated UEC monolayer, and FIG. 3A a confocal micrograph of untreated porcine sperm after 10 min co-incubation with cultivated porcine foetal fibroblasts (porc. foet. F), in FIG. 3B a confocal micrograph of untreated procine sperm after 10 min co-incubation with porcine aortal endothelial cells (pAEC), in FIG. 4A a confocal micrograph of UEC after pre-treatment with sWGA after 10 min co-incubation with porcine sperm, and FIG. 4B a confocal micrograph of UEC after pre-treatment with WGA after 10 min co-incubation with porcine sperm.

EXAMPLE 1: ENHANCING FERTILITY BY BLOCKING BINDING SITES ON SPERM

According to the first variant, binding sites of sperm participating in the binding to uterine epithelial cells (UEC) were identified and blocked, then sperm was co-incubated with cultivated UEC, showing reduced binding of sperm to UEC.

Confluent UEC were grown on glass cover slips form primary cell cultures. In total, uteri from 78 primiparous German Landrace or German Edelschwein gilts aged 8-10 months and with live weights of over 110 kg, were retrieved to harvest primary cells. All animals were maintained and handled according to the German regulations for animal welfare. Gilts were monitored for natural oestrus and slaughtered according to standing heat, i.e. at the time when artificial insemination would have been performed. Gilts were stunned electrically and subsequently slaughtered by exsanguination. Three minutes after bleeding the abdomen was opened and the uterus removed in toto. Further, the ovaries, oviducts and the mesometrium were removed by cutting with sterile scissors without damaging the myometrium. The uterine horns were ligated with stitching thread between and a section of 20-25 cm was cut off. The sections were placed in sterile phosphate buffered saline (PBS) without $Ca^{++}$ and $Mg^{++}$ (Karl Roth, Karlsruhe, Germany) containing 2% Penicillin/Streptomycin (P/S; PAA, Pasching, Austria) in a glass bottle and kept at 5° C. for 45 min. After 45 min at 5° C. the uterine sections were removed from the bottle and placed on cellulose tissue under a sterile laminar flow system. The stitching material was removed. Each horn was fixed with sterile artery clamps ensuring open ends and the lumen was then rinsed three times with 10 ml sterile PBS containing 2% P/S using a 10 ml sterile serological pipette. One end was then shut by a clamp and 10 ml ethylene diamine tetraacetic acid and Trypsin (EDTA/Try; 10% (PAA, Pasching, Austria) in PBS without $Ca^{++}/Mg^{++}$) were inserted via a 10 ml sterile serological pipette into the horn and the remaining end equally closed with a clamp. Subtle movement of the horn ensured equal distribution throughout the lumen. Incubation took place in fresh 20 ml plain PBS containing 2% P/S at 37° C. for 15 min. After enzymatic digestion 10 ml of PBS were added, the horn moved subtly and the liquid caught in a 50 ml centrifuge tube containing 5 ml of warm cell culture medium (D20, 77% DMEM, 20% FBS, 1% Na-pyruvate, 1% amino acids, 1% P/S). The cell suspension was centrifuged for 4 min at 209× g and RT. This procedure was performed three times per horn with a difference in digestion time of ten instead of 15 min for the second and third repeat. After centrifugation the supernatant was removed by aspiration and the cell pellet was gently resuspended in 500 µl of 37° C. warm D20 medium. Cells from both horns were pooled and disseminated onto the glass coverslips coated with collagen in a 6-well culture dish and cultured in an incubator at 5% $CO_2$ saturation at 37° C. with humidified atmosphere. Glass cover slips (22 mm diameter, Karl Roth, Karlsruhe, Germany) were thinly coated with rat tail collagen type-I (Becton Dickinson Biosciences, Heidelberg, Germany) diluted to 50 µg/ml in 0.02 M acetic acid in sterile PBS (without $Ca^{++}$ and $Mg^{++}$). One cover slip was placed in each well of the six-well dish and 600 µl collagen solution were carefully pipetted onto each coverslip to form a convex meniscus and incubated at room temperature (RT) for one hour. Remaining liquid was then removed by aspiration and the matrices were used for dissemination of cells. Uterine epithelial cells were harvested, disseminated and cultured in cell culture medium (D20) containing modified whole Dulbecco's modified Eagle's medium DMEM (containing 2 mmol L-Glutamine (Applichem, Darmstadt, Germany) and 0.1 mmol β-mercapto ethanol (Sigma Aldrich, Darmstadt, Germany) supplemented with 20% heat-inactivated fetal bovine serum, 1% Modified Eagle's Medium (MEM) non-essential amino acids, 1% P/S (all PAA, Pasching, Austria) and 1% sodium pyruvate (Sigma Aldrich, Darmstadt, Germany). For dissemination of the cells 15 µg/ml endothelial cell growth factor (ECGF, ReliaTech, Wolfsburg, Germany) were added. After two days 2 ml fresh D20 medium (containing no ECGF) were added to the cells without removing the old media. This ensured complete adhesion of cells and no removal by aspiration of floating cells. After five days the old media was removed completely and replaced by 2 ml per well of fresh medium every three days.

For identification of epithelial cells, cell culture medium was removed from confluent UEC and the cells were washed with plain PBS and fixed with 1 ml iced methanol (MeOH; 80%; Karl Roth, Karlsruhe, Germany) per well for 10 min. Methanol was removed and 1 ml blocking solution (2% donkey serum in plain PBS) per well was added and incubated at room temperature for 15 min. The cells were washed twice subsequently for 5 min with plain PBS., immune-fluorescence antibody staining was made using an epithelial cell-specific monoclonal rat antibody (Troma III-s; rat anti-cytokeratin-19; Developmental Studies Hybridoma Bank, Iowa, USA) as a primary antibody, specific for cytokeratin-19 (KRT-19), which is an intermediate filament protein responsible for the structural integrity of epithelial cells. The primary antibody was applied at dilutions of 1:100, 1:200 and 1:500 in PBS and Triton (10×; Merck, Darmstadt, Germany) to the fixed cells and incubated for 24 h in a moist chamber at 5° C. Unbound antibody was removed by washing the cells with 1 ml plain PBS per well three times. As a secondary antibody, goat anti-Mouse IgG (H+L), AlexaFluor® 555 conjugate, MoBiTec, Göttingen, Germany) was applied at 1:2000 dilution and incubated for 60 min at 37° C. The secondary antibody was removed by washing the cells twice with 1 ml of plain PBS per well and for the third rinse 1 ml bisbenzimide H 33342 trichydrochloride (H$_{\text{OECHST}}$-33342; 0.1 mg/ml in $H_2O$; Sigma Aldrich, Steinheim) was applied and incubated for 10 min at room temperature. Subsequently, the cells were fixed one more time with iced MeOH (80%). For detection with a fluorescent microscope (Olympus BX 60, Olympus, Hamburg, Germany) equipped with a high resolution digital camera (Olympus DP 71, Olympus, Hamburg, Germany), coverslips were removed from the wells and were placed on microscopic slides upside down onto mounting media (VectaShield®, Vector Laboratories, California, USA) and fixed with clear nail varnish along the outer edge. For detection UV light and a rhodamine filter (555-565 nm) as well as bright field were used. This analysis confirmed that cultivated cells were UEC.

Confluent UEC grown on glass cover slips, as described above, were used. For comparison, confluent porcine aortal endothelial cells (PAEC) as well as porcine foetal fibroblasts (foet. F) were used. The binding specificity of porcine spermatozoa to the porcine endometrium was confirmed by the reduced binding to the comparative cells. The fibroblasts where used as an inter-species, but non-surface cell type, to prove whether sperm bind to any kind of cell or tissue in the same intensity as to porcine UEC. Porcine aortal endothelia represent a lumen cell from a non-reproductive organ. These cell types are isolated as described by Boquest et al., Biol. Reprod 60, 1013-1019 (1999).

Sperm was collected from four verifiably fertile boars (German Landrace and German Edelschwein). To ensure constant semen quality, the service boars were collected for semen regularly twice a week with two to three days interval. The sperm-rich fraction was collected by the gloved-hand method and carefully extended with same parts with warm D20 medium. Sperm concentration was measured using a NukleoCounter® NC-100™ (ChemoMetec A/S, Allerod, Denmark), and the sample was examined for motility, membrane integrity and morphological changes.

The sperm concentration was determined using a NukleoCounter® NC-100™ (ChemoMetec A/S, Allerød, Denmark) and membrane integrity was measured flow-cytometrically using a FACScan© using propidium iodide staining. Motility was determined using an IVOS-sperm-analysis system (Hamilton Thorne Biosciences, Beverly, Mass., USA). Ejaculates with ≤70% motile spermatozoa were dismissed. Semen was then extended to a concentration of $100 \times 10^6$ sperm cells/ml and washed twice by centrifugation (10 min, 800× g, RT) to remove the seminal plasma. The supernatant was discarded and the pellet was resuspended in D20 medium.

To identify possible seminal plasma effects, UEC were also incubated with epididymal sperm of four (German Edelschwein) known fertile boars. For epididymal sperm, the testes were removed by castration and the seminiferous tubules were dissected from the testes and the caudal epididymes were flushed with warm D20 medium and epididymal sperm were extended to $100 \times 10^6$/ml, respectively. It could therefore be excluded that seminal plasma components, already attached to the sperm surface, have influence on binding to UEC. Semen was diluted to $100 \times 10^6$/ml in D20 medium and incubated with one of the following lectins WGA, sWGA, or ConA by incubation with a dilution of 1 µl of the lectin in 200 µl PBS (without $Ca^{++}$ and $Mg^{++}$) to gain a concentration of 10 µg/ml. Fifteen microliters of this lectin dilution were added to 100 µl of sperm and incubated for 15 min at 37° C. in an incubator. Unbound lectin was removed by washing (4 min, 800× g, RT) and resuspending the pellet in D20.

As a control for binding, ejaculated porcine sperm was labelled with FITC-labelled lectins WGA, sWGA, ConA or RCA120, using flow-cytometer tubes (Greiner bio-one, Frickenhausen, Germany) prepared with 480 µl PBS (without $Ca^{++}$ and $Mg^{++}$) and 3 µl PI each. After completed incubation, 20 µl sperm-lectin solution were added and incubated for further ten minutes at RT. As a control one aliquot of the sperm suspension was treated identically without a lectin. Strong binding was observed in FACS analysis as given below, wherein the glycan ligand is listed, for which the lectin has predominant affinity:

| lectin | glycan ligand | fluorescence intensity (mean ± standard deviation) |
|---|---|---|
| WGA | N-acetyl-glucosamine sialic acid | 917.27 ± 332.74 |
| sWGA | N-acetyl-glucosamine | 553.46 ± 153.99 |
| ConA | mannose/glucose | 260.25 ± 122.15 |
| RCA120 | β-D-Gal-D-galactosamine | 151.56 ± 71.18 |

These results show that these lectins have strong binding to the sperm cells, indicating the presence of N-acetyl-glucosamine, sialic acid, mannose and glucose, and of β-D-Gal-D-galactosamine on ejaculated porcine sperm.

The semen that was pre-incubated with one of the lectins was added to confluent UEC and analysed by confocal microscopy.

For the co-incubation with UEC, 500 µl of lectin pre-incubated sperm were released onto a UEC monolayer and the binding activity observed under a phase contrast microscope (Olympus BX 60, Olympus, Hamburg, Germany) equipped with a high resolution digital camera (Olympus DL 70, Olympus, Hamburg, Germany). The binding density was quantified by area under view and compared to results from the control incubation with untreated sperm. Images (2 repeats/boar and lectin) were divided into fields of 61.6 µm² and the fields with and without sperm were counted.

FIG. 1 shows the microscopic picture of control sperm (not treated, in D20 medium) incubated with UEC, showing strong binding of the sperm cells to UEC. Results are shown in FIG. 2A for sperm after pre-incubation with ConA, in FIG. 2B after pre-incubation with WGA. For control, sperm was treated in parallel but without lectin. Analysis of sperm binding to the cultivated cell layer was by a manual area-under-view method, wherein images were taken at 200× magnification and graded into squares of 61.6 µm² size. The area covered with and without sperm was quantified. Five images per boar were taken and evaluated. The area evaluation was performed by the same person throughout all experiments. Control sperm bound at 18050.25±5520.06 µm², WGA-pre-treated sperm bound at 2362.87±248.61 µm² and sWGA-pre-treated sperm bound at 1684.83±107.94 µm², showing a significant reduction in binding to UEC by the pre-treatment with WGA and sWGA. Sperm pre-treated with ConA (affine for mannose/glucose) bound at 12718.39±1999.52 µm², showing a significant reduction in binding, although reduced to a smaller extent than by pre-incubation with WGA or sWGA.

The binding of untreated sperm was repeated using epididymal sperm instead of ejaculated sperm (control). The binding intensity was found to be equivalent.

For analysis of sperm binding to other cells than UEC, cell culture medium was removed from the confluent monolayers of UEC porcine foetal fibroblasts or porcine aortal endothelial cells, each growing on collagen coated coverslips, and 500 µl sperm suspension ($100 \times 10^6$/ml) of either ejaculated or caudal epididymal sperm were applied to each well. Co-incubation took place for up to 60 min in an incubator (37° C., 8% $CO_2$), preferably at ten minutes of incubation as this period was identified to be sufficient. Subsequently, remaining sperm were removed carefully by aspiration and the monolayer was washed gently with warm D20 cell culture medium. The coverslip was mounted onto a microscopic slide with the cells and sperm facing upwards and a 200 µl droplet of D20 was pipetted onto the cover slip to protect the cells from drying out. Sperm binding was viewed under a phase contrast microscope (Olympus GX 60, Olympus, Hamburg, Germany) connected to a high resolution digital camera (Olympus DP71, Olympus, Hamburg, Germany). The image and video documentation was performed with the CellP® software (Version 1.0, Olympus, Hamburg, Germany). The result is shown in FIG. 3A for porcine foetal fibroblasts (porc. foet. F), in FIG. 3B (sperm heads stained with Hoechst-33342) for porcine aortal endothelial cells (pAEC). Analysis of binding intensity showed a significantly (p=0.002) lower binding intensity of untreated sperm to fibroblasts (3018.4±638.1 µm$^2$) compared to UEC (15923.6±2657.9 µm$^2$), and a significantly lower binding intensity to pAEC (2797.8±593.4 µm$^2$). This shows that the binding of sperm to UEC is cell-type specific.

These results show that blocking the binding sites on the sperm by a binding agent having affinity for N-acetyl glucosamine and/or affinity for sialic acid as exemplified by the lectin WGA and/or for mannose/glucose as exemplified by the lectin ConA reduces the binding of sperm to the endometrium, and hence increases the number of sperm available for fertilisation, e.g. at the oviduct or ampulla.

EXAMPLE 2: ENHANCING FERTILITY BY BLOCKING BINDING SITES FOR SPERM ON UEC

Confluent UEC were washed twice with 1 ml PBS (without Ca++ and Mg++) and 45 µl lectin suspension (10 µg/ml) of one of the four selected lectins (WGA, sWGA, PNA, ConA) and incubated for 15 min at 37° C. at 8% $CO_2$ in an incubator. Subsequently, the lectin solution was aspirated and cells washed gently with 1 ml PBS (without Ca++ and Mg++) and 500 µl of sperm (100×10$^6$ sperm/ml) were released onto the UEC monolayer and incubated for 10 min. Binding activity was observed under a phase contrast microscope (Olympus, BX 60, Olympus, Hamburg, Germany) equipped with a high resolution digital camera (Olympus DL 70, Olympus, Hamburg, Germany) and the density was estimated.

Figure 4A:
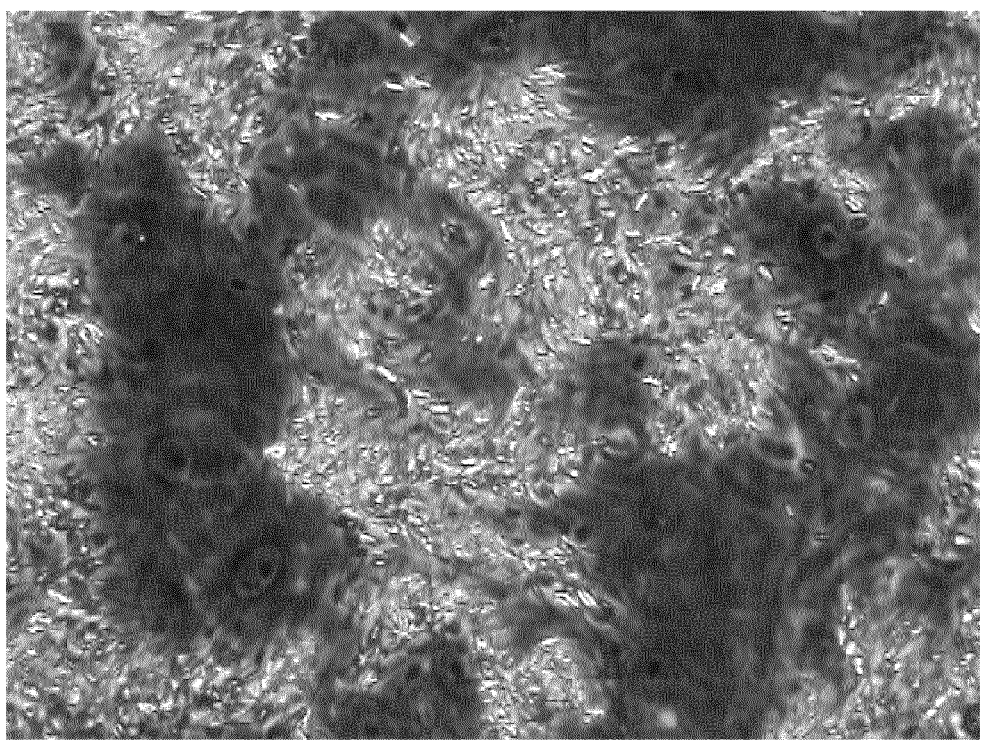
Figure 4B:
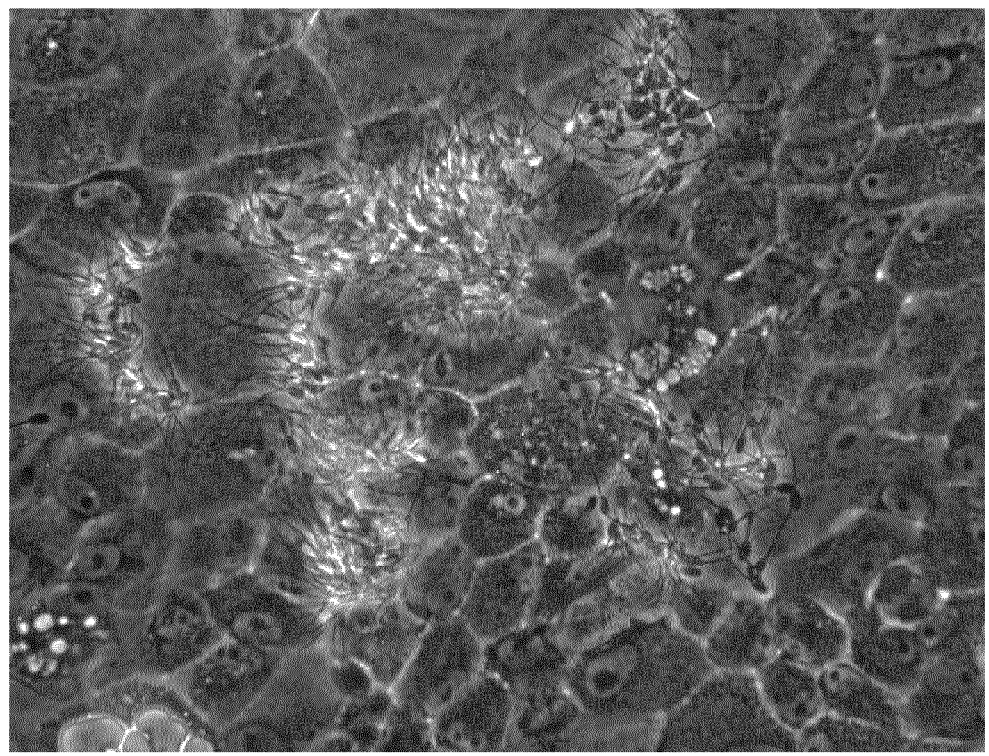

FIG. 4A shows a micrograph of UEC pre-incubated with sWGA after incubation with porcine sperm cells diluted in D20 medium, FIG. 4B a micrograph of UEC pre-incubated with WGA after incubation with porcine sperm cells diluted in D20 medium. Sperm binding density was significantly (p<0.05) lower on UEC pre-incubated with WGA (affinity for Glc-NAc/sialic acid; 5961±309.18 µm$^2$) compared to untreated control UEC cells (17426.81.4±4653.58 µm$^2$). Furthermore, treatment with sWGA (having affinity for Glc-NAc) and ConA (having affinity for mannose/glucose) did not significantly impair sperm binding.

This result shows that blocking the sialic acid on UEC, e.g. by an agent having affinity for sialic acid, or removal of the sialic acid ligand from UEC reduces the binding of sperm to the endometrium, and hence increases the number of sperm available for fertilisation, e.g. at the oviduct or ampulla.

After pre-incubation of UEC with PNA (affinity for β-D-(1-3)-D-galactosamine) some areas showed massive sperm binding as seen with untreated UEC, whereas others were not populated at all, similar to WGA-treated UEC.

EXAMPLE 3: ENHANCING FERTILITY BY BLOCKING BINDING SITES

For artificial fertilisation sows were uses as an example of a female mammal Generally, sows were inseminated at standing heat, and again 12 h later, each time using either 50×10$^6$, 100×10$^6$, 500×10$^6$ or 1000×10$^6$ freshly diluted sperm for the insemination-. For comparison, a comparison group of sows were inseminated with fresh sperm at a dose of 3 billion sperm in commercially available standard diluent.

Each group comprised 4-6 animals. Administration of all compositions was by standard artificial insemination for deposition at the distal part of the uterine body.

A first group of sows was administered the sperm dose in a composition of 10 µg/ml WGA in the standard diluent, a second group of sows was administered a composition of 100 ml standard diluent containing 10 µg/ml WGA, followed after 2 to 20 min by administration of the sperm dose in standard diluent.

Further, sperm from the same boar was sorted into a fraction containing at least 90% X-chromosome bearing sperm using FACS generally according to U.S. Pat. No. 5,135,759 A. The sex-chromosome specific sperm was used without freezing in a third group of sows for control containing the sperm dose in standard diluent only, in a fourth group of sows containing the sperm dose in a composition of WGA in the standard diluent, a fifth group of sows in a composition of 100 ml standard diluent containing 10 µg/ml WGA, followed after 2 to 20 min by administration of the sperm dose in standard diluent.

After 36 d, fertilisation was monitored by ultrasound diagnosis.

In the second groups, fertilisation was significantly increased in comparison to the first control group.

In the fourth to fifth groups, fertilisation was significantly increased in comparison to the third control group, also showing a strong bias for female offspring.

The invention claimed is:

1. A composition for enhancing the fertility of an artificial insemination porcine sperm dose, comprising at least one binding agent, which is a lectin or antibody, the binding agent is not modified by a polyethylene glycol (PEG) moiety, the binding agent having affinity for N-acetyl glucosamine or affinity for sialic acid.

2. The composition according to claim 1, containing porcine sperm in a dose which is lower by a factor of at least 5 compared to the dose for use in conventional artificial insemination, which dose for use in conventional artificial insemination for fresh porcine sperm is a dose of 1 to 3×10$^9$ for fresh sperm, and which dose for use in conventional artificial insemination for frozen porcine sperm is a dose of 5×10$^9$.

3. The composition according to claim 1, wherein the composition is formulated for administration to the genital tract of a gilt or sow prior to or concurrent to the introduction of sperm into the genital tract of the gilt or sow.

4. The composition according claim 1, wherein the composition is formulated for application to the uterus of a gilt or sow.

5. The composition according claim 1, wherein the composition is formulated for insemination of a gilt or sow.

6. A method for providing porcine sperm for use in artificial insemination, comprising contacting the sperm with at least one binding agent, which is a lectin or antibody, the binding agent is not modified by a PEG-moiety, the binding agent having affinity for N-acetyl glucosamine or affinity for sialic acid prior to or concurrent to artificial insemination.

7. The method according to claim 6, wherein the porcine sperm is separated from the at least one binding agent and prior to artificial insemination.

8. The method for preparing a gilt or sow for artificial insemination, comprising administering a composition into the genital tract of the gilt or sow prior to or concurrent to introduction of porcine sperm, the composition comprising at least one binding agent having affinity for N-acetyl glucosamine and/or affinity for sialic acid, which binding agent is a lectin or antibody, the binding agent is not modified by a PEG moiety.

9. The method according to claim 6, wherein introduction of sperm is into the uterus, and wherein concurrent to or following administration of the composition, porcine sperm is introduced into the uterus at a dose of at maximum $0.4 \times 10^9$ for fresh sperm, or at a dose of at maximum $1 \times 10^9$ for frozen sperm.

10. A method for artificial insemination of a gilt or sow with porcine sperm, comprising contacting the sperm with at least one binding agent having affinity for N-acetyl glucosamine and/or affinity for sialic acid, which binding agent is a lectin or antibody, the binding agent is not modified by a PEG moiety, prior to or concurrent to insemination.

11. The method according to claim 10, wherein the porcine sperm is in contact with the binding agent and is introduced into the uterus of the female mammal.

12. The method according to claim 10, wherein the sperm is porcine sperm in a dose of at maximum $0.4 \times 10^9$ fresh sperm, or at a dose of at maximum $1 \times 10^9$ for frozen sperm.

13. An artificial insemination sperm dose containing porcine sperm, comprising the composition according to claim 1.

14. The artificial insemination sperm dose according to claim 13, wherein the porcine sperm is sex-chromosome specific sorted porcine sperm.

15. The insemination sperm dose according to claim 13, wherein the porcine sperm is contained in a dose which is lower by a factor of at least 5 compared to the dose for conventional artificial insemination, which dose for conventional artificial insemination for fresh porcine sperm is a dose of 1 to $3 \times 10^9$ for fresh sperm, and which dose for conventional artificial insemination for frozen porcine sperm is a dose of $5 \times 10^9$.

16. The artificial insemination sperm dose according to claim 15, wherein the porcine sperm is contained in a dose which is lower by a factor of at least 10, compared to the dose for use in conventional artificial insemination.

17. The artificial insemination sperm dose according to claim 15, wherein the porcine sperm is contained in a dose which is lower by a factor of at least 100, compared to the dose for use in conventional artificial insemination.

18. The method according to claim 12, wherein the sperm is porcine sperm in a dose of at maximum $0.2 \times 10^9$ fresh sperm, or at a dose of at maximum $0.5 \times 10^9$ for frozen sperm.

19. The method according to claim 9, wherein the sperm is porcine sperm in a dose of at maximum $0.2 \times 10^9$ fresh sperm, or at a dose of at maximum $0.5 \times 10^9$ for frozen sperm.

* * * * *